(12) United States Patent
Buchanan (10) Patent No.: US 7,695,191 B1
(45) Date of Patent: Apr. 13, 2010

(54) X-RAY IMAGING AND POSITIONER

(76) Inventor: L. Stephen Buchanan, 2335 Foothill La., Santa Barbara, CA (US) 93105

( * ) Notice: Subject to any disclaimer, the term of this patent is extended or adjusted under 35 U.S.C. 154(b) by 266 days.

(21) Appl. No.: 11/633,939

(22) Filed: Dec. 5, 2006

Related U.S. Application Data (60) Provisional application No. 60/720,231, filed on Dec. 5, 2005.

(51) Int. Cl.
*A61B 6/14* (2006.01)
*A61B 6/08* (2006.01)

(52) U.S. Cl. .................... 378/170; 375/38; 375/206

(58) Field of Classification Search ............ 378/38–40, 378/168, 170, 191, 204–206; 433/29–31, 433/49–67, 140, 229; D24/152, 176
See application file for complete search history.

(56) References Cited

U.S. PATENT DOCUMENTS

| | | | | |
|---|---|---|---|---|
| RE25,773 | E | * | 5/1965 | Medwedeff et al. ......... 378/170 |
| 4,012,638 | A | * | 3/1977 | Altschuler et al. ......... 378/170 |
| 5,327,477 | A | * | 7/1994 | Levy ......................... 378/168 |
| 7,090,395 | B2 | * | 8/2006 | Glazer ....................... 378/191 |
| 7,278,787 | B2 | * | 10/2007 | Hack et al. ................. 378/206 |
| 2005/0185767 | A1 | * | 8/2005 | Puente et al. .............. 378/168 |

* cited by examiner

*Primary Examiner*—Irakli Kikadze
*Assistant Examiner*—Anastasia Midkiff (57) ABSTRACT

An apparatus for use in positioning and obtaining of x-ray and other images of teeth and related structures, providing the practitioner with increased ease and accuracy of aiming, greatly simplified instrument configuration with significantly reduced number and complexity of the instruments employed, while providing patients with improved comfort and control during the imaging process.

17 Claims, 7 Drawing Sheets

X-RAY IMAGING AND POSITIONER

REFERENCE TO RELATED APPLICATION

This is a non-provisional application from provisional application Ser. No. 60/720,231, filed Dec. 5, 2005, with claim of priority therefrom.

BACKGROUND OF THE INVENTION

1. Field of the Invention

This invention relates to the field of dentistry and, more particularly, to improvements in apparatus for creating x-ray images of teeth in the patient's mouth.

2. Description of the Related Art

Customer users (dentists and dental assistants) of dental radiographic imaging devices have three primary requirements of any system they use. These requirements are for accuracy of image (both in position and angle), speed of image capture, and ease of placing and securing the image capture device in the patient's mouth. I am aware of at least seven ways that existing systems do not optimally answer those requirements—problems which are all resolved with the device of my invention.

First, the bite plates on the well-known Rinn XCP devices to hold the film/sensor positioners in place are difficult to insert into small mouths, as they are quite long and are at right angles to the film/sensor. It requires patients to open widely, retraction of the tongue when imaging mandibular teeth, and a certain gymnastic rotational movement to get the positioner in place.

Second, they are impossible to use when a rubber dam clamp is on the tooth to be imaged, and although holders such as the EndoRay™ (designed for rubber dam applications) can be placed under the dam and around the clamp and files, it is a very difficult thing to do.

Third, bite-plate positioners usually cause foreshortening artifacts when imaging maxillary teeth, due to the tipping of the positioner and x-ray beam when the film edge encounters a less-than-high palate. For both anterior and posterior maxillary x-rays, a cotton roll must be placed between the tooth to be imaged and the bite plate, to drop the film angle closer to the horizontal.

Fourth, while most of the known positioners have rings to allow correct aiming of the x-ray beam onto the film/sensor, only the recently introduced Gendex™ device has an aiming device to center the tooth in question on the image surface. Without this type of aiming device, it is difficult to correctly place the positioner when capturing angled views.

Fifth, most of the positioners require three different bite plate holders (anterior, posterior, and bitewing), two different rods, and three different aiming rings to match the holders—eight parts in total. It is very inconvenient to have to inventory and disinfect all of these parts, as well as to assemble three parts each time a tray set-up is made.

Sixth, while digital x-ray sensors most elegantly solve the speed issue, nearly all of them are wired to remote computers/processors, creating difficulties from the resulting tethering effect. While dentists who use wired sensors are used to this inconvenience, there is no dentist who, all things being equal, would not choose a wireless sensor instead. Today's high-tech dental operatories already have a mass of cords and tubing to step on; removing the wire from sensors is not only more convenient, but also reduces the chances of damaging an expensive sensor by eliminating the chance of stepping on the cord and rocketing the sensor to the floor.

Seventh, the only known wireless sensor has three disadvantages; high cost, thick sensors, and poor consistency of wireless signal.

SUMMARY OF THE INVENTION

The Wireless Film/Sensor Positioner of my invention satisfies each of the three requirements and answers all seven of the current challenges associated with current imaging devices.

First and foremost, my positioner has no bite plate. The two greatest advantages of my positioner having no bite plate are ease of insertion and reduction of foreshortening artifacts when using it for maxillary imaging. My holder, without the right-angle bite plate, allows easy insertion of the horizontally oriented film or sensor between the patient's teeth and into their mouth, after which it is easily rotated into its final position, parallel to the long axis of the tooth to be imaged. Because it has no bite plate positioned at the edge of the film and because of its adjustable arm, it can be placed ideally in palatal vaults for the vertical angle needed to portray the maxillary roots in their correct proportions without the use of a cotton roll. Because it has an adjustable arm and aiming ring, it requires no extra parts to shoot anterior, posterior, or bitewing images.

Second, the positioner is held in place by the patient holding a large handle similar to kitchen tool handles designed for arthritic patients, around which patients can wrap their whole hand. While this flies in the face of current dogma that the patient should never hold a positioner to steady it during the x-ray exposure, I have found it to be the rare exception when a patient cannot perform this function. My device does have a removable rubber bite block which can be attached to the shank end of the holder arm for disabled patients to bite on; however, its position is away from the tooth to be imaged.

While this handle is empty for positioners that only hold film, it also acts as a container for the batteries and transmitter needed for a wireless sensor. The thinnest sensors are harder for patients to tolerate than film and very importantly, this allows for a minimal thickness of the sensor. Locating the battery and transmitter on the sensor is not necessary, as all digital x-ray sensors must be held in place by a positioner. The size of the handle, being much greater than the space available on the side of the sensor, allows for a larger battery with longer life as well as allowing for fewer miniaturization challenges for the engineers designing the transmitter. With the larger size of transmitter board, development and manufacturing costs should be lower; and the functionality of the transmitter may be improved, for instance, by adding a frequency scanner to avoid interference from other electronic devices in the office.

The handle also allows for an aiming light, powered by the same battery, to be placed adjacent to the aiming ring. The aiming ring has in its center a folded reflective mylar surface element that directs the aiming light beam at the tooth to be imaged. This insures that the tooth being looked at is always captured in the center of the image.

The positioner is designed for quick and effective infection control procedures. The aiming ring is removable so that it can be placed in a disinfection solution. The sensor, the arm, and the handle are easily covered with a plastic sleeve, so those sensitive electronic parts do not need to be autoclaved.

While the non-electronic film holder version of my positioner will be more expensive than traditional film holders, the greatly improved functionality of a frequently used device will justify that higher price. In the case of the wireless sensor positioner the ease of use, the more predictable wireless image transmission, and the reduced cost of design and manufacturing should not only allow capture of most of the wireless imaging market, but will become an engine of growth for that market.

BRIEF DESCRIPTION OF THE DRAWINGS

A better understanding of the present invention may be realized from a consideration of the following detailed description, taken in conjunction with the accompanying drawings, in which.

DETAILED DESCRIPTION OF THE PREFERRED EMBODIMENTS

Figure 1:
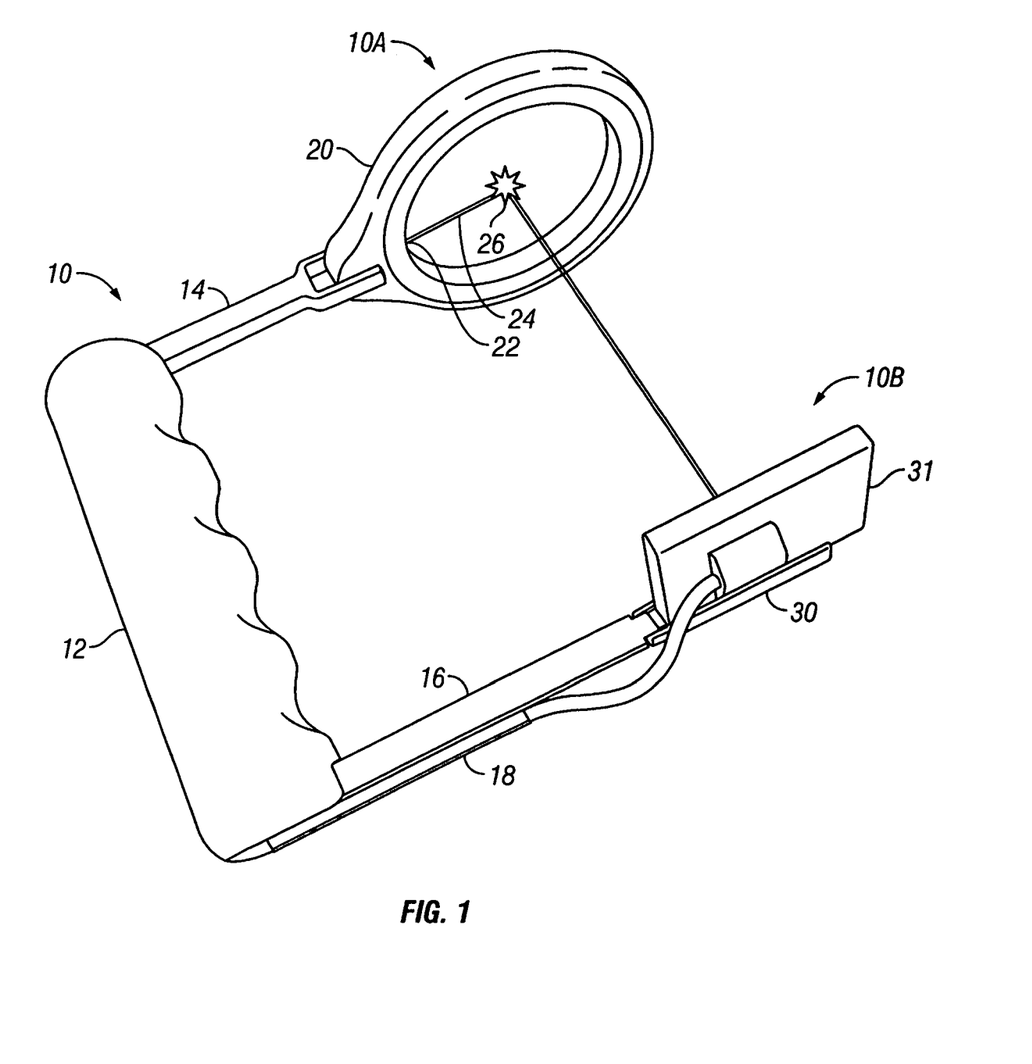
FIG. 1 is a schematic view of one particular arrangement in accordance with the invention.

FIG. 1 illustrates an apparatus 10 for positioning and imaging x-ray films or sensors, comprising an aiming portion 10A and a sensor positioning portion 10B, connected to, and separated by, a holding assembly 12.

Holding assembly 12 may be of a shape, material, and texture to provide a comfortable and functional handle for gripping. The holding assembly 12 serves to provide a convenient means for grasping the apparatus 10 and orienting aiming portion 10A and sensor positioning portion 10B. In addition, holding assembly 12 also serves as a structure for mounting aiming portion 10A and sensor positioning portion 10B, while providing appropriate separation and orientation. Finally, holding assembly 12 may be constructed so as to be at least partially hollow, thereby providing space for containing the batteries and electrical components (not shown) for the apparatus 10.

Aiming stand-off arm 14 is fixed adjacent to, and in between, aiming portion 10A and holding assembly 12.

Sensor stand-off arm 16 is fixed adjacent to, and in between, sensor positioning portion 10B and holding assembly 12.

It is preferable if aiming arm 14 and sensor arm 16 extend from holding assembly 12 generally parallel to each other, and generally perpendicular to holding assembly 12.

Aiming portion 10A comprises a positioning ring 20, an aiming guide 22 which projects aiming beam 24, and a beam reflector 26. Positioning ring 20 is pivotably mounted to aiming arm 14 opposite holding assembly 12. Positioning ring 20 is pivotable along a plane generally parallel to the sensor. Aiming guide 22 is mounted within, or on, positioning ring 20 such that the generated aiming beam 24 emanates toward the center of positioning ring 20. Beam reflector 26 is mounted in the center of positioning ring 20 and is angled such that aiming beam 24 is redirected toward the sensor.

Sensor positioning portion 10B comprises sensor attachment bracket 30, which is adapted to receive and retain x-ray or other film, phosphor plates, a wireless transmitter, or other sensors. Sensor attachment bracket 30 is pivotably mounted to sensor arm 16 opposite holding assembly 12. Sensor arm 16 may be equipped with wire harness 18 to retain and guide wires connecting a sensor to electrical components contained within holding assembly 12. Sensor attachment bracket 30 is pivotable along a plane generally parallel to aiming portion 10A, and perpendicular to aiming beam 24. after it has been redirected by beam reflector 26 toward the sensor.

Positioning ring 20 and sensor attachment bracket 30 are both equipped with corresponding detents, or stops, along their pivotable paths. These detents are preset to correspond with the more commonly used instrument configurations encountered by the practitioner, thereby making it faster and easier to set up the instrument for different configurations. Through the provision of such matching detents, the instrument of the present invention ensures the proper alignment and orientation of the sensor with respect to an x-ray or other energy source.

In addition to the benefits set forth above, the apparatus of the present invention presents the practitioner with the ability to have one instrument satisfy all of the varied configurations necessary to image a patient's teeth, thereby greatly reducing the number of implements and devices currently used in performing this task.

Figure 2:
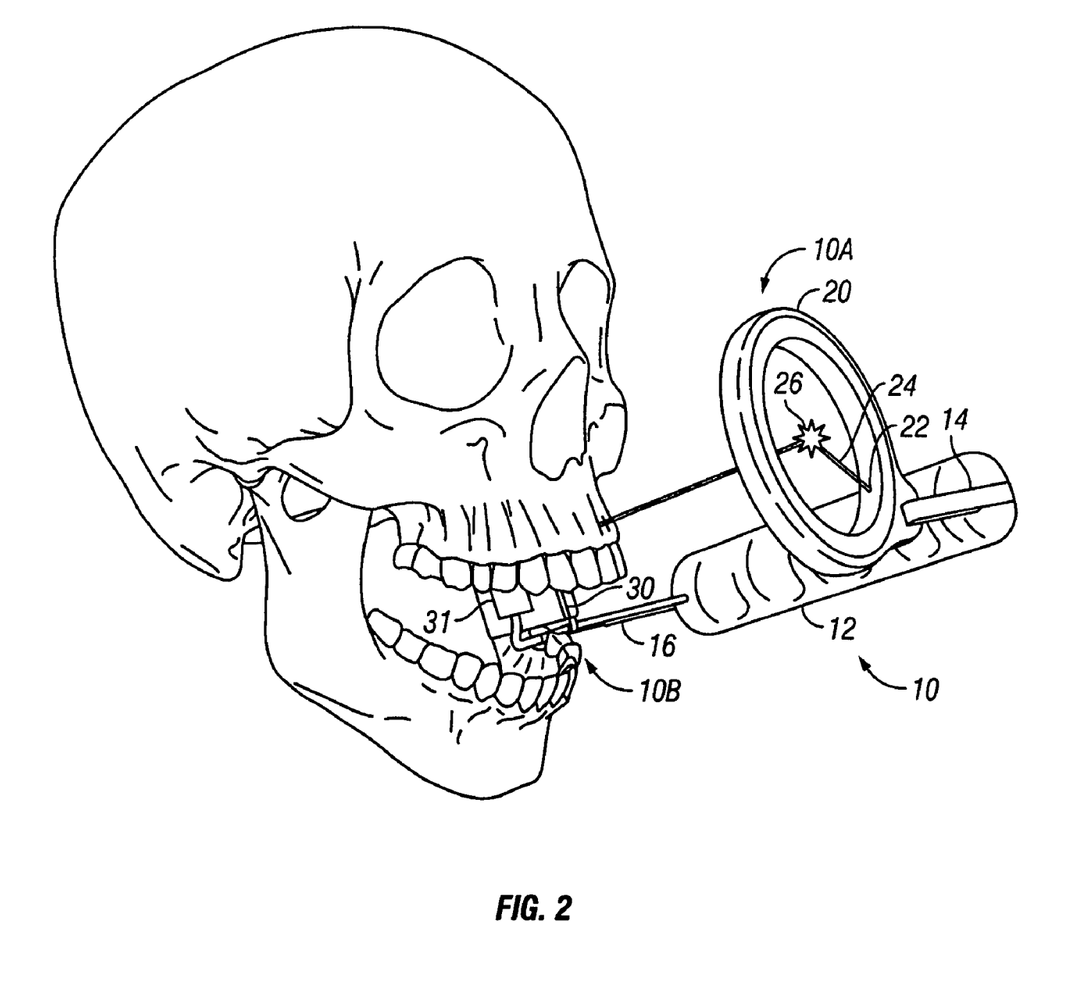
FIG. 2 is a schematic view of the arrangement of FIG. 1 being portrayed as used to obtain anterior maxillary x-ray images on a model anatomical human skull.

FIG. 2 illustrates the use of apparatus 10 to obtain anterior maxillary images on a model anatomical skull. Positioning ring 20 and sensor attachment bracket 30 are depicted as being pivoted in the maxillary direction in order to facilitate the imaging. A sensor 31 is depicted being held in sensor attachment bracket 30. Aiming beam 24, emitted by aiming guide 22, is shown being redirected by beam reflector 26, located at the center of positioning ring 20, toward the sensor. With the sensor positioned inside the mouth, aiming beam 24 strikes and illuminates the anterior maxillary portion of the jaw that is to be imaged.

Figure 3:
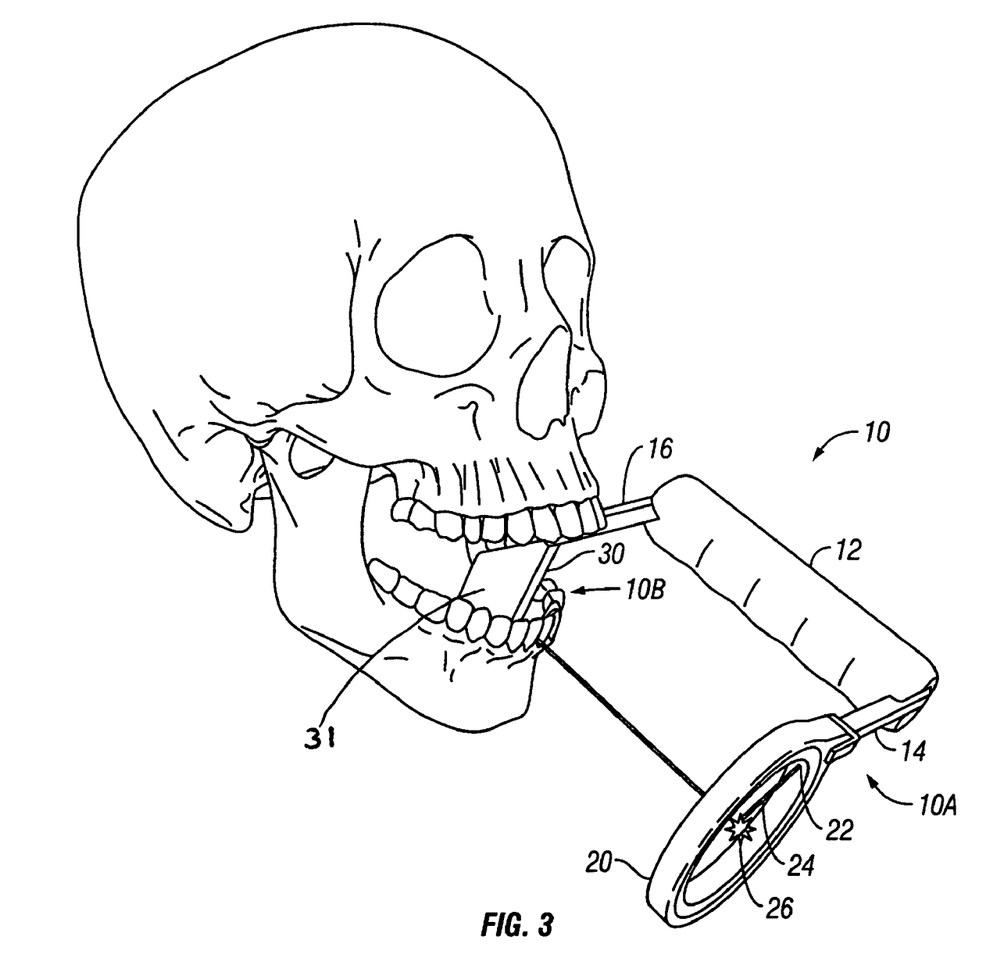
FIG. 3 is a schematic view of the arrangement of FIG. 1 being portrayed as used to obtain anterior mandibular x-ray images on a model anatomical human skull.

FIG. 3 illustrates the use of apparatus 10 to obtain anterior mandibular images on a model anatomical skull. Positioning ring 20 and sensor attachment bracket 30 are depicted as being pivoted in the mandibular direction in order to facilitate the imaging. A sensor 31 is depicted being held in sensor attachment bracket 30. Aiming beam 24, emitted by aiming guide 22, is shown being redirected by beam reflector 26, located at the center of positioning ring 20, toward the sensor. With the sensor positioned inside the mouth, aiming beam 24 strikes and illuminates the anterior mandibular portion of the jaw that is to be imaged.

Figure 4:
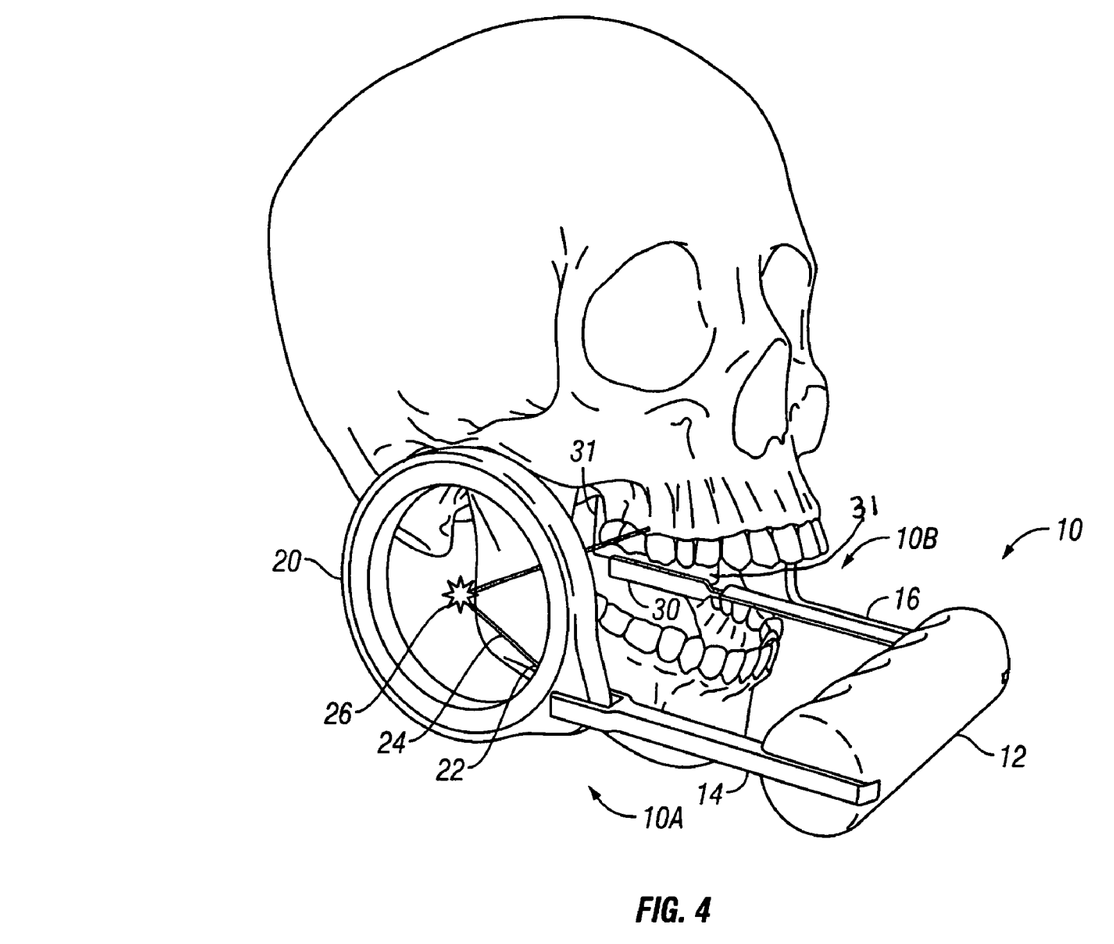
FIG. 4 is a schematic view of the arrangement of FIG. 1 being portrayed as used to obtain posterior maxillary x-ray images on a model anatomical human skull.

FIG. 4 illustrates the use of apparatus 10 to obtain posterior maxillary images on a model anatomical skull. Positioning ring 20 is depicted as being pivoted slightly in the maxillary direction to facilitate the imaging. Sensor attachment bracket 30 is depicted as being in its neutral position in order to facilitate the imaging. A sensor 31 is depicted being held in sensor attachment bracket 30. Aiming beam 24, emitted by aiming guide 22, is shown being redirected by beam reflector 26, located at the center of positioning ring 20, toward the sensor. With the sensor 31 positioned inside the mouth, aiming beam 24 strikes and illuminates the posterior maxillary portion of the jaw that is to be imaged.

Figure 5:
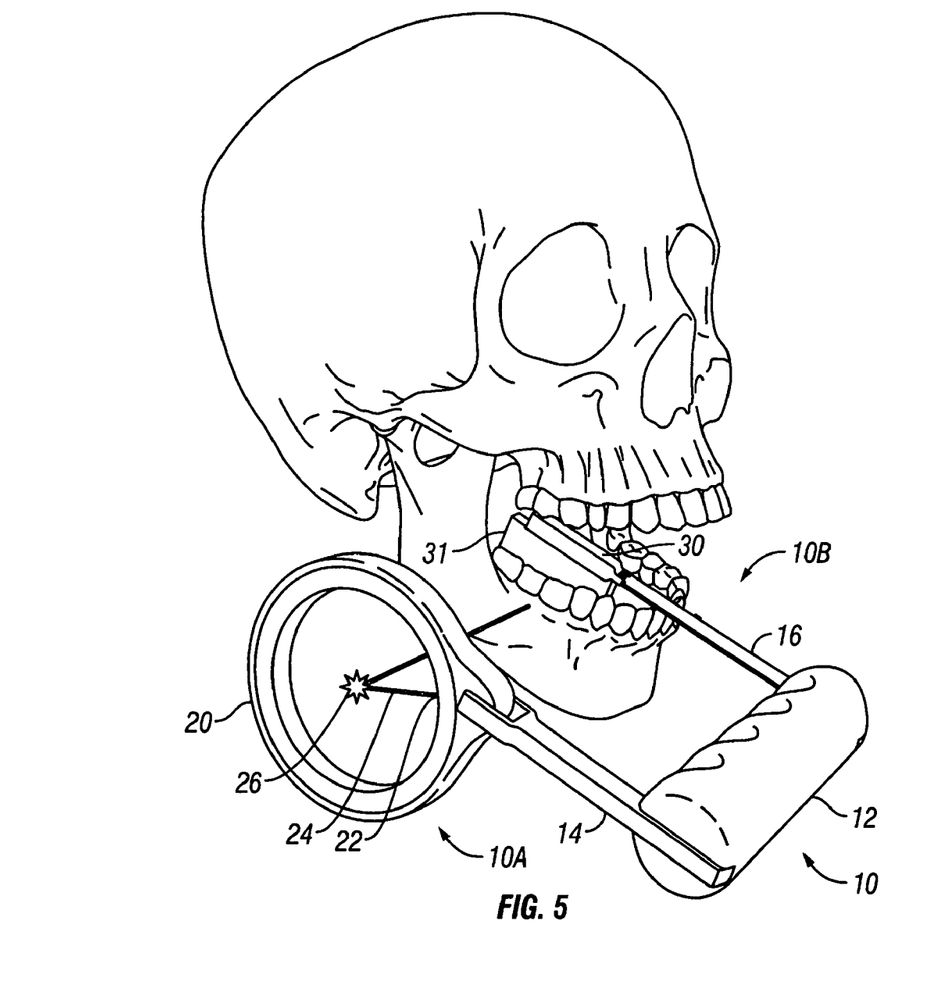
FIG. 5 is a schematic view of the arrangement of FIG. 1 being portrayed as used to obtain posterior mandibular x-ray images on a model anatomical human skull.

FIG. 5 illustrates the use of apparatus 10 to obtain posterior mandibular images on a model anatomical skull. Positioning ring 20 is depicted as being pivoted slightly in the mandibular direction to facilitate the imaging. Sensor attachment bracket 30 is depicted as being in its neutral position in order to facilitate the imaging. A sensor 31 is depicted being held in sensor attachment bracket 30. Aiming beam 24, emitted by aiming guide 22, is shown being redirected by beam reflector 26, located at the center of positioning ring 20, toward the sensor. With the sensor 31 positioned inside the mouth, aiming beam 24 strikes and illuminates the posterior mandibular portion of the jaw that is to be imaged.

Figure 6:
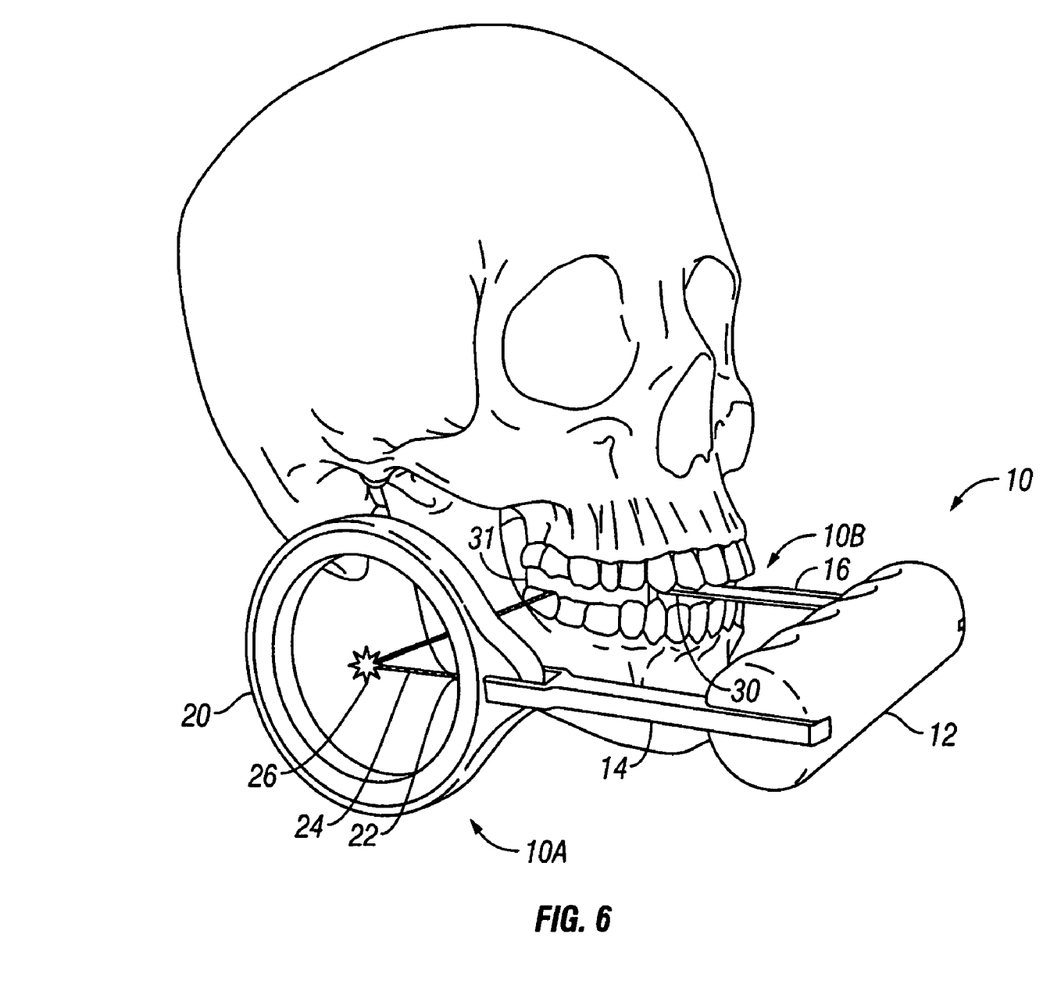
FIG. 6 is a schematic view of the arrangement of FIG. 1 being portrayed as used to obtain bitewing x-ray images on a model anatomical human skull.

FIG. 6 illustrates the use of apparatus 10 to obtain bitewing images on a model anatomical skull. Positioning ring 20 and sensor attachment bracket 30 are depicted as being in their respective neutral positions, in order to facilitate the imaging. A sensor 31 is depicted being held in sensor attachment bracket 30. Aiming beam 24, emitted by aiming guide 22, is shown being redirected by beam reflector 26, located at the center of positioning ring 20, toward the sensor 31. With the sensor positioned inside the mouth, aiming beam 24 strikes and illuminates the bitewing portion of the jaw that is to be imaged.

Figure 7:
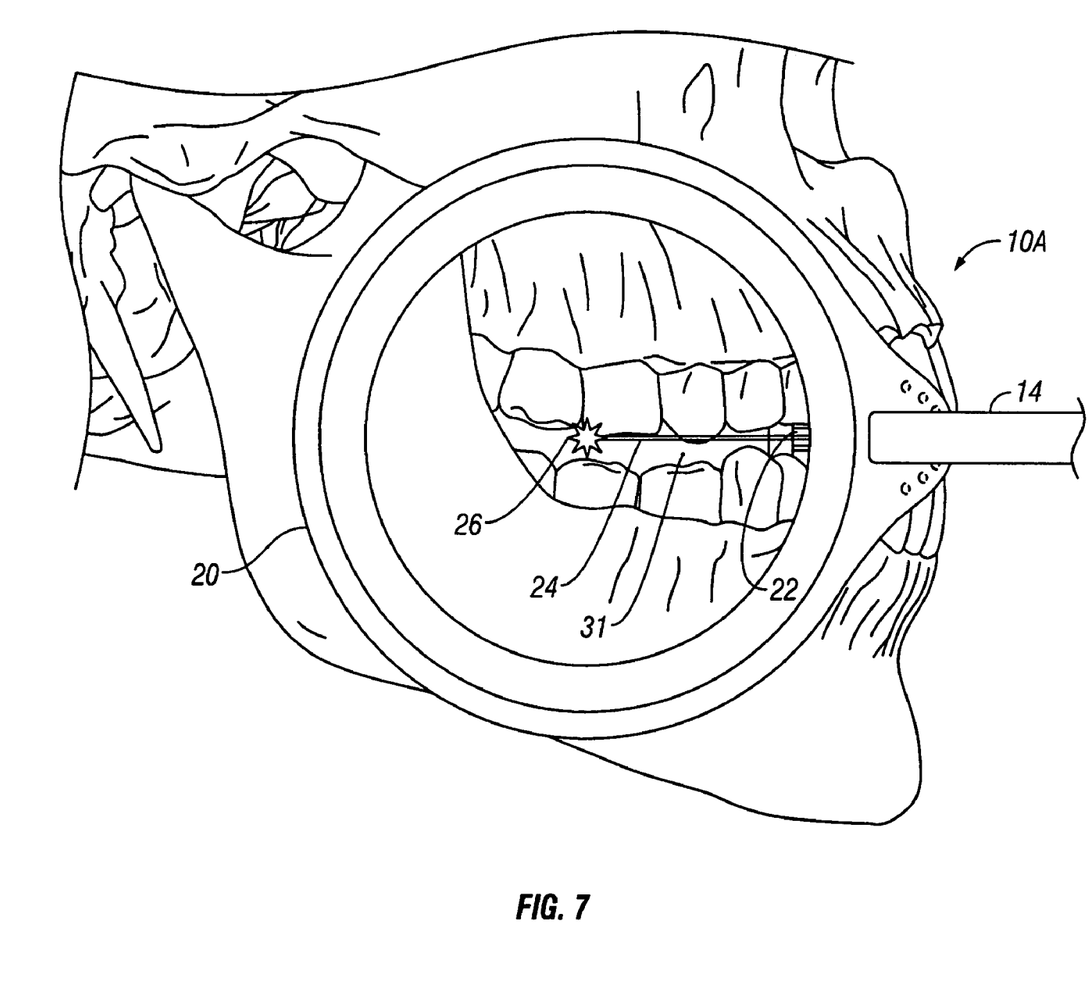
FIG. 7 is a close-up, clinician's view via the aiming portion of the arrangement of FIG. 1 as portrayed in FIG. 6, partially broken away to better show detail.

FIG. 7 illustrates the aiming portion 10A as it would be viewed by a clinician during actual use immediately prior to obtaining images of the bitewing portion of the jaw, as shown in FIG. 6. Aiming beam 24, shown emanating from aiming guide 22 mounted within positioning ring 20, is redirected toward the target area by beam reflector 26, located in the center of positioning ring 20, and illuminates the target area on the sensor 31. The sensor 31 is only partially visible, as it is positioned and contained within the jaw to be imaged.

In the practice of embodiments of the invention, it becomes possible to conveniently and accurately position sensors within patients' mouths. The positioning ring and aiming beam enable simple and accurate verification of the portion to be imaged, while the pivotability of the sensor attachment bracket and positioning ring provide convenient and rapid means for this single versatile implement to effectively replace and surpass an entire collection of instruments which are presently in use for producing x-ray images of teeth.

Although there have been described hereinabove various specific arrangements of an IMPROVED X-RAY IMAGING AND POSITIONER in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. Aiming apparatus for use in developing x-ray images of teeth in the mouth of a patient, comprising:
a holding assembly shaped to serve as a handle for gripping the apparatus;
an aiming portion coupled to a first end of the holding assembly by a pivotable mounting which is oriented to maintain the aiming portion in a first plane;
said aiming portion being generally circular in shape and having a beam reflector generally centrally mounted therein;
a sensor positioning portion coupled to a second end of the holding assembly, remote from the first end, by a second pivotable mounting member which is oriented to maintain the sensor positioner in a plane parallel to said first plane: a sensor mounted at said sensor positioning portion to receive a redirected beam from said reflector; and
a beam generator for generating a beam to be directed radially inward toward said beam reflector and then redirected thereby toward said sensor.

2. Apparatus for generating and directing an aiming beam for use in the production of images on x-ray films or sensors located within a dental patient's mouth, the apparatus comprising:
a portable holding assembly including:
an aiming portion which is generally circular in shape and has a beam reflector generally centrally mounted therein, said beam reflector being adapted to redirect a received beam toward sensor positioning portion;
a sensor positioning portion having sensing means mounted thereon for receiving said redirected beam;
a handle for manually grasping the assembly; and
coupling means for coupling the aiming portion and the sensor positioning portion to the handle in parallel orientation to each other.

3. The apparatus of claim 2, wherein the handle is fabricated in a shape which is suitable for manually gripping the assembly.

4. The apparatus of claim 3, wherein the handle is at least partially hollow to provide space for a power supply and electrical components for generating aiming beam.

5. Apparatus for generating and directing an aiming beam for use in the production of images on x-ray films or sensors located within a dental patient's mouth, the apparatus comprising:
a portable holding assembly including:
an aiming portion;
a sensor positioning portion having sensing means mounted thereon;
a handle for manually grasping the assembly; and
coupling means for coupling the aiming portion and the sensor positioning portion to the handle in parallel orientation to each other,
wherein the aiming portion includes a generally circular positioning ring having an aiming guide mounted near the periphery of the positioning ring for directing an aiming beam radially inward from the periphery; and further including a beam reflector positioned at the center of the ring for redirecting the beam to the sensor positioning portion.

6. The apparatus of claim 2, wherein the means for coupling the aiming portion to the handle includes a pivotable link to permit the aiming portion to pivot in a plane which is generally orthogonal to the handle.

7. The apparatus of claim 2, wherein the means for coupling the sensor positioning portion to the handle includes a pivotable link to enable the sensor positioning portion to pivot in a plane which is generally orthogonal to the handle.

8. The apparatus of claim 2, wherein the coupling means for coupling the aiming portion and the sensor positioning portion to the handle include corresponding pivotable links which enable the aiming portion and the sensor positioning portion to pivot in planes which are generally parallel to each other.

9. The apparatus of claim 8, wherein the pivotable links are respectively coupled to corresponding standoff arms mounted at opposite ends of the handle.

10. The apparatus of claim 9, wherein the respective standoff arms are generally parallel to each other.

11. The apparatus of claim 5, wherein the generally circular positioning ring includes a beam reflector and means for mounting said beam reflector generally centered within the positioning ring for redirecting the beam toward the sensor positioning portion.

12. The apparatus of claim 2, wherein the sensor positioning portion includes a sensor attachment bracket for mounting the sensing means thereon.

13. The apparatus of the claim 12, further including a wire harness having electrical wires connecting the sensing means to electrical components contained within the handle.

14. Apparatus for use in aiming X-ray apparatus to develop x-ray images of teeth in the mouth of a dental patient, comprising:

a handle having first and second opposing ends;

a circular aiming portion coupled to the first end of the handle and oriented in a first plane orthogonal thereto;

a sensor-positioning portion coupled to the second end of the handle and adapted to hold an x-ray beam receptor in a second plane orthogonal to the handle and parallel to said first plane but displaced therefrom;

a beam generator located on the circumference of the circular aiming portion for generating an aiming beam to be directed to the sensor-positioning portion; and a reflector mounted in the center of said circular aiming portion to redirect said aiming beam toward said sensor positioning portion.

15. The apparatus of claim 14 further including a pivotable mounting means for coupling the aiming portion to the handle, said mounting means being adapted to pivot the aiming portion to different positions in said first plane.

16. The apparatus of claim 14 wherein the mounting means coupling the sensor-positioning portion to said handle is adapted to pivot the sensor-positioning portion only to different positions in said second plane.

17. The apparatus of claim 15 wherein the mounting means coupling the sensor positioning portion to said handle is adapted to pivot the sensor-positioning portion only to different positions in said second plane.

* * * * *